US008309351B2

(12) United States Patent
Kremmidiotis et al.

(10) Patent No.: US 8,309,351 B2
(45) Date of Patent: Nov. 13, 2012

(54) METHODS OF IDENTIFYING AGENTS THAT INHIBIT ANGIOGENESIS

(75) Inventors: Gabriel Kremmidiotis, Flagstaff Hill (AU); Annabell Francis Leske, Allenby Gardens (AU)

(73) Assignee: Bionomics Limited, Thebarton, SA (AU)

( * ) Notice: Subject to any disclaimer, the term of this patent is extended or adjusted under 35 U.S.C. 154(b) by 0 days.

(21) Appl. No.: 12/681,311

(22) PCT Filed: Oct. 2, 2008

(86) PCT No.: PCT/AU2008/001467
§ 371 (c)(1),
(2), (4) Date: Jun. 24, 2010

(87) PCT Pub. No.: WO2009/043104
PCT Pub. Date: Sep. 4, 2009

(65) Prior Publication Data
US 2010/0285497 A1      Nov. 11, 2010

(30) Foreign Application Priority Data

Oct. 4, 2007   (AU) ............................... 2007905437

(51) Int. Cl.
*C12N 5/071*  (2010.01)
*C12N 5/07*   (2010.01)
*C12N 5/00*   (2006.01)

(52) U.S. Cl. .......................... 435/371; 435/363; 435/325

(58) Field of Classification Search .................. None
See application file for complete search history.

(56) References Cited

U.S. PATENT DOCUMENTS

| | | | |
|---|---|---|---|
| 4,708,871 | A | 11/1987 | Geysen |
| 4,833,092 | A | 5/1989 | Geysen |
| 5,223,409 | A | 6/1993 | Ladner et al. |
| 5,403,484 | A | 4/1995 | Ladner et al. |
| 5,556,762 | A | 9/1996 | Pinilla et al. |
| 5,571,689 | A | 11/1996 | Heuckeroth et al. |
| 5,663,143 | A | 9/1997 | Ley et al. |
| 5,750,373 | A | 5/1998 | Garrard |
| 5,969,108 | A | 10/1999 | McCafferty et al. |
| 2004/0110241 | A1 | 6/2004 | Segal |
| 2007/0134161 | A1* | 6/2007 | Brown ............................ 424/9.6 |
| 2010/0292190 | A1* | 11/2010 | Chaplin et al. .................. 514/94 |

FOREIGN PATENT DOCUMENTS

| | | |
|---|---|---|
| WO | WO84/03506 | 9/1984 |
| WO | WO84/03564 | 9/1984 |
| WO | WO00/00823 | 1/2000 |
| WO | WO00/08139 | 2/2000 |
| WO | WO00/39585 | 7/2000 |
| WO | WO01/46455 | 6/2001 |
| WO | WO2006/128027 | 11/2006 |
| WO | WO2008/011513 | 1/2008 |

OTHER PUBLICATIONS

Kremmidiotis et al. 2005. Expert Opin. Ther. Targets: 9:211-215.*
Alessandri G et al., "Mobilization of Capillary Endothelium in Vitro Induced by Effectors of Angiogenesis in Vivo", Cancer Res., vol. 43, pp. 1790-1797 (1983).
Dellian et al., "Quantitation and Physiological Characterization of Angiogenic Vessels in Mice", Am. J. Pathol., vol. 149, pp. 59-72 (1996).
Denizot F and Lang R, 1986, "Rapid colorimetric assay for cell growth and survival—Modifications to the tetrazolium dye procedure giving improved sensitivity and reliability", J. Immunol. Methods 89: 271-277.
Dudar TE and Jain RK, "Microcirculatory Flow Changes during Tissue Growth", Microvasc. Res., vol. 25, pp. 1-21 (1983).
Frapolli et al, "Pharmacokinetics and Metabolism in Mice ofIDN 5390 (I3-(N-Boc-3-i-butylisoserinoyl)-C-7,8-seco-I O-deacetylbaccatin III), aNew Oral C-seco-Taxane Derivative with Antiangiogenic Property Effective on Paclitaxel-Resistant Tumors", Drug Metabolism and Disposition, vol. 34, No. 12, pp. 2028-2035 (Dec. 2006).
Genbank Accession No. NM_001069, Aug. 3, 2010.
Genbank Accession No. NM_006086, Jul. 25, 2010.
Genbank Accession No. NM_006087, Aug. 3, 2010.
Genbank Accession No. NM_006088, Jul. 25, 2010.
Genbank Accession No. NM_030773, Jul. 25, 2010.
Genbank Accession No. NM_032525, Aug. 3, 2010.
Genbank Accession No. NM_177987, Mar. 5, 2010.
Genbank Accession No. NM_178012, Aug. 1, 2010.
Genbank Accession No. NM_178014, Aug. 3, 2010.
Genbank Accession No. NP_001060, Aug. 3, 2010.
Genbank Accession No. NP_006077, Jul. 25, 2010.
Genbank Accession No. NP_006078, Aug. 3, 2010.
Genbank Accession No. NP_006079, Jul. 25, 2010.
Genbank Accession No. NP_110400, Jul. 24, 2010.
Genbank Accession No. NP_115914, Aug. 3, 2010.
Genbank Accession No. NP_817124, Mar. 5, 2010.
Genbank Accession No. NP_821080, Aug. 1, 2010.
Genbank Accession No. NP_821133, Aug. 3, 2010.
Gerlowski L and Jain RK, "Microvascular Permeability of Normal and Neoplastic Tissues", Microvasc. Res., vol. 31, pp. 288-305 (1986).

(Continued)

*Primary Examiner* — Shulamith H Shafer
(74) *Attorney, Agent, or Firm* — Jenkins, Wilson, Taylor & Hunt, P.A.

(57) ABSTRACT

The presently disclosed subject matter relates to the identification of markers of endothelial cells which are in a quiescent or activated state, and more specifically to beta tubulin isotypes as markers which are differentially expressed between endothelial cells in these states. The beta tubulin isotypes can be used for the identification of candidate agents which selectively bind quiescent or activated endothelial cells, and to identify candidate agents which inhibit or promote angiogenesis and/or vascular function.

2 Claims, 3 Drawing Sheets

OTHER PUBLICATIONS

Gimbrone MAJ et al., "Tumor Growth and Neovascularization: An Experimental Model Using the Rabbit Cornea", J. Natl. Cancer Inst., vol. 52, pp. 413-427 (1974).

Guckelberger et al., "Beneficial effects of CD39Iecto-nucleoside triphosphate diphosphohydrolase-I in murine intestinal ischemia-reperfusion injury", Thrombosis and Haemostasis, vol. 91, No. 3, pp. 576-586 (Mar. 2004).

Hallak et al., "Targeted Measles Virus Vector Displaying Echistatin Infects Endothelial Cells via avp3 and Leads to Tumor Regression", Cancer Research, vol. 65, No. 12, pp. 5292-52300 (Jun. 15, 2005).

International Preliminary Report on Patentability corresponding to International Application No. PCT/AU2008/001467 dated Apr. 7, 2010.

International Search Report corresponding to International Application No. PCT/AU2008/001467 dated Dec. 8, 2008.

Kanzawa S, "Improved In Vitro Angiogenesis Model by Collagen Density Reduction and the Use of Type III Collagen", Ann. Plast. Surg., vol. 30, pp. 244-251 (1993).

Lawley TJ and Kubota Y, "Induction ofMorphologic Differentiation of Endothelial Cells in Culture", J. Invest. Dermatol., vol. 93, pp. 59S-61S (1989).

Liang P et al., "Differential Display of Eukaryotic Messenger RNA by Means of the Polymerase Chain Reaction", Science, vol. 257 (5072), pp. 967 (1992).

Lisitsyn NA et al., Cloning the Differences Between Two Complex Genomes, Science, vol. 259 (5097), p. 946 (1993).

Muthukkaruppan and Auerbach, "Angiogenesis in the Mouse Cornea", Science, vol. 205, pp. 1416-1418 (1979).

Muthukkaruppan VR et al., "The Chick Embryo Aortic Arch Assay: A New, Rapid, Quantifiable In Vitro Method for Testing the Efficacy of Angiogenic and Anti-Angiogenic Factors in a Three-Dimensional, Serum-Free Organ Culture System", Proc. Am. Assoc. Cancer Res., vol. 41, p. 65 (2000).

Nguyen M et al., "Quantitation of Angiogenesis and Antiangiogenesis in the Chick Embryo Chorioallantoic Membrane", Microvasc. Res., vol. 47, pp. 31-40 (1994).

Nicosia RF and Ottinetti A, "Growth of Microvessels in Serum-Free Matrix Culture of Rat Aorta—A Quantitative Assay of Angiogenesis In vitro", Lab. Invest., vol. 63, pp. 115-122 (1990).

Oikawa T et al., "Effects of Cytogenin, a Novel Microbial Product, on Embryonic and Tumor Cell-Induced Angiogenic Responses in Vivo", Anticancer Res., vol. 17, pp. 1881-1886 (1997).

Pepper MS et al., "Transforming Growth Factor-Beta 1 Modulates Basic Fibroblast Growth Factor-induced Proteolytic and Angiogenic Properties of Endothelial Cells in Vitro", J. Cell Biol., vol. 111, pp. 743-755 (1990).

Plunkett ML and Hailey JA, "Methods in Laboratory Investigation An In vivo Quantitative Angiogenesis Model Using Tumor Cells Entrapped in Alginate", Lab. Invest., vol. 62, pp. 510-517 (1990).

Ribatti D et al., "The chick embryo chorioallantoic membrane as a model for in vivo research on angiogenesis", Int. J. Dev. Biol., vol. 40, pp. 1189-1197 (1996).

Rice et al., "Development of a High Volume Screen to Identify Inhibitors of Endothelial Cell Activation", Analytical Biochemistry, vol. 241, No. 2, pp. 254-259 (Oct. 15, 1996).

Schena M et al., "Quantitative Monitoring of Gene Expressing Patterns with a Complementary DNA Microarray", Science, vol. 270(5235), p. 467 (1995).

Scott JK and Smith GP, "Searching for Peptide Ligands with an Epitope Library", Science, vol. 249, p. 386 (1990).

Semba T et al., "An Angiogenesis Inhibitor E7820 Shows Broad-Spectrum Tumor Growth Inhibition in a Xenograft Model: Possible Value of Integrin α2 on Platelets as a Biological Marker", Clin. Cancer Res., vol. 10, pp. 1430-1438 (2004).

Shelanski ML et al., "Microtubule Assembly in the Absence of Added Nucleotides", PNAS, vol. 70, pp. 765-768 (1973).

Staton CA et al., "Current methods for assaying angiogenesis in vitro and in vivo", Int. J. Path., vol. 85, pp. 233-248 (2004).

Staton CA et al., "Alphastatin, a 24-amino acid fragment of human fibrinogen, is a potent new inhibitor of activated endothelial cells in vitro and in vivo", Blood, vol. 103, pp. 601-606 (2004).

Stribbling SM et al., "Regressions of Established Breast Carcinoma Xenografts by Carboxypeptidase G2 Suicide Gene Therapy and the Prodrug CMDA Are Due to a Bystander Effect", Hum. Gene. Ther., vol. 11, pp. 285-292 (2000).

Sullivan KF and Cleveland DW, "Identification of conserved isotype-defining variable region sequences for four vertebrate f8 tubulin polypeptide classes", PNAS USA, vol. 83(12), pp. 4327-4331 (1986).

Tercel M et al., "Unsymmetrical DNA Cross-Linking Agents: Combination of the CBI and PBD Pharmacophores", J. Medicinal. Chem., vol. 46, pp. 2132-2151 (2003).

Velculescu VE et al., "Serial Analysis of Gene Expression", Science, vol. 270 (5235), p. 4484 (1995).

Wang D et al., "The Mammalian β-Tubulin Repertoire: Hematopoietic Expression of a Novel, Heterologous β-Tubulin Isotype", J. Cell Biol., vol. 103 (5), pp. 1903-1910 (1996).

Wemme H et al., "Measurement of Lymphocyte Proliferation: Critical Analysis of Radioactive and Photometric Methods", Immunobiology, vol. 185, pp. 78-79 (1992).

Yonekura K et al., "UFT and Its Metabolites Inhibit the Angiogenesis Induced by Murine Renal Cell Carcinoma, as Determined by a Dorsal Air Sac Assay in Mice", Clin. Cancer Res., vol. 5, pp. 2185-2191 (1999).

Belleri et al., "Antiangiogenic and vascular-targeting activity of the microtubule-destabilizing trans-resveratrol derivative 3,5,4'-trimethoxystilbene", Molecular Pharmacology, vol. 67, No. 5, pp. 1451-1459 (May 2005).

Cooney et al., "Drug Insight: Vascular disrupting agents and angiogenesis—Novel approaches for drug delivery," Nature Clinical Practice Oncology, vol. 3, No. 12, pp. 682-692 (Jan. 2006).

European Search Report corresponding to European Patent Application No. 08800102.9-2401 / 2205971 PCT/AU2008001467 dated Mar. 2, 2011.

Gong et al., "In vivo and in vitro evaluation of erianin, a novel anti-angiogenic agent", European Journal of Cancer, vol. 40, No. 10, pp. 1554-1565 (Jul. 2004).

Micheletti et al., "Vascular-targeting activity of ZD6126, a novel tubulin-binding agent", Cancer Research, vol. 63, No. 7, pp. 1534-1537 (Apr. 2003).

Bonne D et al., 1985, J. Biol. Chem. 280(5):2819-2825.
Brown NJ et al., 2002, Br. J. Cancer 86: 1813-1816.
Dark G et al., 1997, Cancer Res. 57:1829-1834.
Davis P et al., 2002, Cancer Res. 62:7247-7253
Kremmidiotis G et al., 2010, Mol. Cancer Ther. 9(6):1562-1573.
Leunig M et al., 1992, Cancer Res. 62: 6553-6560.
Levasseur JE et al., 1975, Stroke 6: 308-317.
Lopata MA and Cleveland DW, 1987, J. Cell Biol. 105(4): 1707-1720.
Mahadevan V et al., 1989, Cancer Res. 49: 415-419.

\* cited by examiner

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ccccatacat accttgaggc ga                                            22

<210> SEQ ID NO 2
<211> LENGTH: 20
<212> TYPE: DNA
<213> ORGANISM: Artificial Sequence
<220> FEATURE:
<223> OTHER INFORMATION: primer
```

```
<400> SEQUENCE: 2
gccaaaagga cctgagcgaa                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgagggaga tcgtgcacat                                               20

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
cccctgagcg gacactgt                                                 18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aggggctaac aatggacacc                                               20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
ccgaagataa gggggaacta ct                                            22
```

METHODS OF IDENTIFYING AGENTS THAT INHIBIT ANGIOGENESIS

FIELD

The present invention relates to the identification of markers of endothelial cells which are in a quiescent or activated state, and more specifically to beta tubulin isotypes as markers which are differentially expressed between endothelial cells in these states. The beta tubulin isotypes can be used for the identification of agents which selectively bind quiescent or activated endothelial cells, and to identify agents which inhibit or promote angiogenesis and/or vascular function. Such agents are therefore useful in the treatment of angiogenesis-related disorders. The beta tubulin isotypes can also be used to predict a response to a therapeutic and/or can monitor disease progression.

BACKGROUND

Angiogenesis, the formation of new blood vessels from existing vasculature, is known to be associated with a number of pathological conditions, including rheumatoid arthritis, diabetic retinopathy, and psoriasis, and is also an essential process for local tumour progression and the development of distant metastasis.

The formation of new capillaries is a multistep process which is controlled by positive and negative factors as well as by complex interactions between tumour cells, host endothelium, stromal cells, and extracellular matrix components. The process begins with an angiogenic stimulus to existing vasculature, usually mediated by growth factors such as vascular endothelial growth factor or basic fibroblast growth factor. This is followed by degradation of the extracellular matrix, cell adhesion changes and disruption, an increase in cell permeability, and activation of endothelial cells, e.g. proliferation of endothelial cells and their migration towards the site of blood vessel formation.

Later stages of angiogenesis include vessel lumen formation, stabilisation and differentiation by the migrating endothelial cells, basement membrane production, and the induction of vessel bed specializations. The final stages of vessel formation include what is known as remodelling, wherein a forming vasculature becomes a stable, mature vessel bed.

However, in the (normal) healthy adult, angiogenesis is virtually arrested and occurs only when needed, such as in wound healing, hair growth, renewal of the endometrium during the menstrual cycle, formation and growth of the corpus luteum during pregnancy, and in the restoration of tissue structure and function after injury.

There is therefore a need in the art to identify markers which allow endothelial cells that are participating in the process of angiogenesis (activated endothelial cells) to be distinguished from those endothelial cells which are not (quiescent endothelial cells). This is important not only for the detection of diseases or conditions associated with angiogenesis, but will allow the identification of agents that bind preferentially to activated or quiescent endothelial cells.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art, in Australia or in any other country.

SUMMARY

In a first aspect the invention provides the use of a beta tubulin isotype that is differentially expressed between activated endothelial cells and quiescent endothelial cells for identifying an agent which inhibits or promotes angiogenesis and/or vascular function.

In one embodiment, expression of the beta tubulin isotype is higher in activated endothelial cells when compared to quiescent endothelial cells, and the use identifies an agent which inhibits angiogenesis and/or vascular function.

In another embodiment, expression of the beta tubulin isotype is higher in quiescent endothelial cells when compared to activated endothelial cells, and the use identifies and agent which promotes angiogenesis and/or vascular function.

In a second aspect the invention provides the use of an activated endothelial cell for identifying an agent which inhibits angiogenesis and/or vascular function, by assaying for interaction of the agent with a beta tubulin isotype which displays higher expression in activated endothelial cells when compared to expression in quiescent endothelial cells.

In a third aspect the invention provides the use of a quiescent endothelial cell for identifying an agent which promotes angiogenesis and/or vascular function, by assaying for interaction of the agent with a beta tubulin isotype which displays higher expression in quiescent endothelial cells when compared to expression in activated endothelial cells.

In a fourth aspect the invention provides the use of a beta tubulin isotype that is differentially expressed between activated endothelial cells and quiescent endothelial cells for identifying an agent which selectively interacts with the activated or quiescent endothelial cells.

In one embodiment of the fourth aspect of the invention, expression of the beta tubulin isotype is higher in activated endothelial cells when compared to quiescent endothelial cells, and the use identifies an agent which selectively interacts with activated endothelial cells.

In another embodiment of the fourth aspect of the invention, expression of the beta tubulin isotype is higher in quiescent endothelial cells when compared to activated endothelial cells, and the use identifies an agent which selectively interacts with quiescent endothelial cells.

In a fifth aspect the invention provides the use of a beta tubulin isotype which has higher expression in activated endothelial cells when compared to expression in quiescent endothelial cells, as a marker of activated endothelial cells.

In a sixth aspect the invention provides the use of a beta tubulin isotype which has higher expression in quiescent endothelial cells when compared to expression in activated endothelial cells, as a marker of quiescent endothelial cells.

In one embodiment of the fifth and sixth aspects of the invention, the marker can be used to predict a response to a therapeutic and/or to monitor disease progression.

In a seventh aspect the invention provides a method of identifying an agent which selectively interacts with activated endothelial cells or quiescent endothelial cells, comprising:

(a) providing a beta tubulin isotype which is differentially expressed between activated endothelial cells and quiescent endothelial cells;

(b) adding a candidate agent to the beta tubulin isotype in (a); and (c) assaying for the binding of the candidate agent to the beta tubulin isotype, wherein a candidate agent which binds to the beta tubulin isotype, is an agent which selectively interacts with activated endothelial cells or quiescent endothelial cells.

In one embodiment of the seventh aspect of the invention, expression of the beta tubulin isotype is higher in activated endothelial cells when compared to quiescent endothelial cells, and the method identifies an agent which selectively interacts with activated endothelial cells.

In another embodiment of the seventh aspect of the invention, expression of the beta tubulin isotype is higher in quiescent endothelial cells when compared to activated endothelial cells, and the method identifies an agent which selectively interacts with quiescent endothelial cells.

In an eighth aspect the invention provides a method of identifying an agent which selectively interacts with activated endothelial cells, comprising:
 (a) providing activated endothelial cells;
 (b) adding a candidate agent to the cells in (a); and
 (c) assaying for the binding of the candidate agent to a beta tubulin isotype which has higher expression in the activated endothelial cells when compared to expression in quiescent endothelial cells,
 wherein a candidate agent which binds to the beta tubulin isotype, is an agent which selectively interacts with activated endothelial cells.

In a ninth aspect the invention provides a method of identifying an agent which selectively interacts with quiescent endothelial cells, comprising:
 (a) providing quiescent endothelial cells;
 (b) adding a candidate agent to the cells in (a); and
 (c) assaying for the binding of the candidate agent to a beta tubulin isotype which has higher expression in the quiescent endothelial cell when compared to expression in activated endothelial cells,
 wherein a candidate agent which binds to the beta tubulin isotype, is an agent which selectively interacts with quiescent endothelial cells.

In a tenth aspect the invention provides a method of identifying an agent which selectively interacts with activated endothelial cells, comprising:
 (a) providing activated endothelial cells;
 (b) adding a candidate agent to the cells in (a); and
 (c) determining the effect of the candidate agent on a functional property of the cells,
 wherein a candidate agent which alters a functional property of the cells, is an agent which selectively interacts with activated endothelial cells.

In an eleventh aspect the invention provides a method of identifying an agent which selectively interacts with quiescent endothelial cells, comprising:
 (a) providing quiescent endothelial cells;
 (b) adding a candidate agent to the cells in (a); and
 (c) determining the effect of the candidate agent on a functional property of the cells,
 wherein a candidate agent which alters a functional property of the cells, is an agent which selectively interacts with quiescent endothelial cells.

In a twelfth aspect the invention provides a method of identifying an agent which inhibits or promotes angiogenesis and/or vascular function, comprising:
 (a) providing a beta tubulin isotype which is differentially expressed between activated endothelial cells and quiescent endothelial cells;
 (b) adding a candidate agent to the beta tubulin isotype in (a); and
 (c) assaying for the binding of the candidate agent to the beta tubulin isotype,
 wherein a candidate agent which binds to the beta tubulin isotype, is an agent which inhibits or promotes angiogenesis and/or vascular function.

In one embodiment of the twelfth aspect of the invention, expression of the beta tubulin isotype is higher in activated endothelial cells when compared to quiescent endothelial cells, and the method identifies an agent which inhibits angiogenesis and/or vascular function.

In another embodiment of the twelfth aspect of the invention, expression of the beta tubulin isotype is higher in quiescent endothelial cells when compared to activated endothelial cells, and the method identifies an agent which promotes angiogenesis and/or vascular function.

In a thirteenth aspect the invention provides a method of identifying an agent which inhibits angiogenesis and/or vascular function, comprising:
 (a) providing activated endothelial cells;
 (b) adding a candidate agent to the cells in (a); and
 (c) assaying the binding of the candidate agent to a beta tubulin isotype which has higher expression in the activated endothelial cells when compared to expression in quiescent endothelial cells,
 wherein a candidate agent which binds to the beta tubulin isotype, is an agent which inhibits angiogenesis and/or vascular function.

In a fourteenth aspect the invention provides a method of identifying an agent which promotes angiogenesis and/or vascular function, comprising:
 (a) providing quiescent endothelial cells;
 (b) adding a candidate agent to the cells in (a); and
 (c) assaying for the binding of the candidate agent to a beta tubulin isotype which has higher expression in the quiescent endothelial cells when compared to expression in activated endothelial cells,
 wherein a candidate agent which binds to the one beta tubulin isotype, is an agent which promotes angiogenesis and/or vascular function.

In a fifteenth aspect the invention provides a method of identifying an agent which inhibits angiogenesis and/or vascular function, comprising:
 (a) providing activated endothelial cells;
 (b) adding a candidate agent to the cells in (a); and
 (c) determining the effect of the candidate agent on a functional property of the cells,
 wherein a candidate agent which alters a functional property of the cells, is an agent which inhibits angiogenesis and/or vascular function.

In a sixteenth aspect the invention provides a method of identifying an agent which promotes angiogenesis and/or vascular function, comprising:
 (a) providing quiescent endothelial cells;
 (b) adding a candidate agent to the cells in (a); and
 (c) determining the effect of the candidate agent on a functional property of the cells,
 wherein a candidate agent which alters a functional property of the cells, is an agent which promotes angiogenesis and/or vascular function.

In an embodiment of the tenth, eleventh, fifteenth and sixteenth aspects of the invention, a functional property of the cells includes any one or more of:
 (a) proliferation of the cells;
 (b) migration of the cells;
 (c) the ability of the cells to form capillaries;
 (d) the ability of the cells to participate in angiogenesis;
 (e) the ability of the cells to maintain cell-to-cell contact;
 (f) the ability of the cells to sustain functional blood vessels; and
 (g) the ability of a beta tubulin isotype present within the cell to polymerise when in the presence of an alpha subunit.

In an embodiment of the first, second, fourth, fifth, seventh, eighth, tenth, twelfth and thirteenth aspects of the invention, the beta tubulin isotype is beta I tubulin.

In an embodiment of the first, third, fourth, sixth, seventh, ninth, eleventh, twelfth and fourteenth aspects of the invention, the beta tubulin isotype is beta III tubulin.

In a seventeenth aspect the invention provides an agent when identified by any one of the seventh to sixteenth aspects of the invention.

DETAILED DESCRIPTION

The inventors have found that expression of beta tubulin isotypes varies between activated and quiescent endothelial cells. Although previous studies have shown that the expression of beta tubulin isotypes varies between normal and cancerous cells, expression differences in endothelial cells has not previously been known or anticipated.

Microtubules are cylindrical structures of the cytoskeleton and are composed of heterodimer subunits of alpha and beta tubulin. In vertebrates, there exists at least seven isotypes of beta tubulin.

As used herein, the term "beta tubulin isotype" is taken to include the seven isotypes of beta tubulin which are currently known and published, those which the present inventors have identified from analysis of the GenBank database of NCBI, and those which are as yet unidentified. Currently known and published beta tubulin isotypes include classes I, II, III, IVa, IVb, V, and VI. The present inventors have identified further human isotypes, namely beta VIII tubulin and a new class II isotype (class IIa). Reference to a "beta tubulin isotype" is also reference to the nucleic acid or polypeptide sequence encoding the isotype. Examples of human beta tubulin isotype nucleic acids and polypeptides include:

Beta I tubulin (Sullivan K F and Cleveland D W, 1986, *PNAS USA* 83(12): 4327-4331)—Genbank Accession Numbers: NM_178014 and NP_821133 respectively;

Beta II tubulin (Sullivan K F and Cleveland D W, 1986, *PNAS USA* 83(12): 4327-4331)—Genbank Accession Numbers: NM_178012 and NP_821080 respectively;

Beta IIa tubulin—Genbank Accession Numbers: NM_001069 and NP_001060 respectively;

Beta III tubulin (Sullivan K F and Cleveland D W, 1986, *PNAS USA* 83(12): 4327-4331)—Genbank Accession Numbers: NM_006086 and NP_006077 respectively;

Beta IVa tubulin (Lopata M A and Cleveland D W, 1987, *J. Cell Biol.* 105(4): 1707-1720)—Genbank Accession Numbers: NM_006087 and NP_006078 respectively;

Beta IVb tubulin (Lopata M A and Cleveland D W, 1987, *J. Cell Biol.* 105(4): 1707-1720)—Genbank Accession Numbers: NM_006088 and NP_006079 respectively;

Beta V tubulin (Lopata M A and Cleveland D W, 1987, *J. Cell Biol.* 105(4): 1707-1720)—Genbank Accession Numbers: NM_032525 and NP_115914 respectively;

Beta VI tubulin (Wang D et al., 1996, *J. Cell Biol.* 103(5): 1903-1910)—Genbank Accession Numbers: NM_030773 and NP_110400 respectively; and Beta VIII tubulin—Genbank Accession Numbers: NM_177987 and NP_817124 respectively.

Isotypes corresponding to classes I and IVb are expressed across a number of tissues, whereas class II is a major component of brain beta tubulin. The expression of classes III and IVa is restricted to nerve tissues, class V is ubiquitously expressed except for the brain, and the class VI isotype is expressed by hematopoietic cells.

The beta tubulin isotypes are preferably in purified form and can be synthesised by recombinant DNA technology which is known in the art. For example, any one of the nucleic acid sequences listed above can be introduced into a host cell. Typically, a host cell is transfected with an expression vector comprising the nucleic acid. A variety of expression vector/host systems may be utilized to contain and express a beta tubulin isotype. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express a beta tubulin isotype polypeptide using various expression vectors including plasmid, cosmid and viral systems such as a vaccinia virus expression system. The invention is not limited by the host cell or vector employed. When large quantities of protein are needed, vectors which direct high levels of expression may be used such as those containing the T5 or T7 inducible bacteriophage promoter.

Alpha and beta tubulin isotypes display varied tissue expression, and vary from each other by substitutions within key amino acids. Individual tubulin isotypes can alter the properties of the microtubule through regulating microtubule function. The variation in expression and different properties associated with each of the tubulin isotypes suggests that individual isotypes may have distinct roles in different tissues. Cancers develop resistance to tubulin binding agents such as docetaxel and paclitaxel by altering the tubulin isotype composition of cells. For example, alterations in the expression of beta I tubulin have been found in taxol-resistant lung cancer cells and the docetaxel-resistant breast cancer cell-line MCF-7. Furthermore, expression of tubulin isotypes beta II, beta III and beta IVa have also been shown to be altered in taxol-resistant lung cancer cells and the MCF-7 breast cancer cell-line.

It has been shown that knock-down of beta III tubulin in lung cancer cells results in a 39% increase in paclitaxel sensitivity, further highlighting the importance that beta III tubulin plays in developing resistance to tubulin-binding agents. It has also been shown that the tubulin-binding agent colchicine has the lowest binding affinity for the beta III isotype, and beta III decreases the rate of microtubule polymerisation in vitro.

The inventors have found that the expression of beta tubulin isotypes varies between activated and quiescent endothelial cells. In further studies, expression of beta I tubulin has been found to be higher in activated endothelial cells when compared to quiescent endothelial cells. Further studies have identified that beta III tubulin expression is higher in quiescent endothelial cells when compared to activated endothelial cells.

Whilst differential expression of beta I and beta III tubulin has currently been shown, other beta tubulin isotypes may be differentially expressed in endothelial cells at different stages of their differentiation and/or life cycle.

A "quiescent" endothelial cell in the context of the present invention is taken to mean an endothelial cell which is involved in maintaining stable blood vessels or capillaries, and which exhibits very low or no proliferative and/or migratory activity. In vitro, a quiescent cell may be obtained by culturing an endothelial cell in basal media or under confluent culture conditions, which would be known in the art. For example, suitable media includes the EBM-2 medium (Clonetics, USA) containing 0.1% GA-1000 (gentamicin, amphotericin-B) and 0.5% fetal bovine serum. No growth supplements are present in the culture medium. Both in vitro and in vivo, a quiescent endothelial cell is usually bound to neighbouring endothelial cells, and is not participating in the process of angiogenesis.

During the process of angiogenesis, endothelial cells become activated upon an angiogenic stimulus to existing vasculature, usually mediated by growth factors such as vascular endothelial growth factor or basic fibroblast growth factor. Therefore in the context of the present invention, an "activated" endothelial cell is a cell which has been stimulated, and is responding, to an angiogenic stimulus. The cell may be proliferating, migrating, or forming capillaries, i.e. an "activated" endothelial cell is an endothelial cell participating in the process of angiogenesis.

In vitro an activated endothelial cell may be obtained by culturing an endothelial cell in a growth-supplemented media. Such media would be know in the art, and include the EGM-2 medium (Clonetics, USA) containing basal EBM-2 medium, hEGF, hydrocortisone, 0.1% GA-1000 (gentamicin, amphotericin-B), 2% fetal bovine serum, vascular endothelial growth factor (VEGF), human fibroblast growth factor beta, $R^3$-insulin growth factor-1, ascorbic acid and heparin.

The activation of endothelial cells leads to changes in expression of one or more genes in these cells when compared to expression of the same one or more genes in quiescent endothelial cells. This is known as "differential expression" and refers to the level, concentration, or activity of a constituent (e.g. a nucleic acid corresponding to a particular gene and/or its encoded protein) in a first sample (or set of samples) as compared to the level or activity of the constituent in a second sample (or set of samples), where the method used for detecting the constituent provides a different level or activity when applied to the two samples (or set of samples). As an example, a protein which is measured at one concentration in a first sample, and at a different concentration in a second sample, is differentially expressed in the first sample as compared with the second sample. Essentially, the protein acts as a marker for distinguishing the two samples from each other. As used herein, the term "marker" is taken to mean "a characteristic that is objectively measured and evaluated as an indicator of normal biological processes, pathogenic processes, or pharmacological responses to therapeutic interventions." (NIH Biomarker Definitions Working Group, 1998). In the context of the present invention, an example of a suitable marker is a beta tubulin isotype nucleic acid and/or its encoded protein. The marker measurement may be higher or increase, or may be lower or decrease, in response to particular biological processes; or, if a marker measurement typically changes in the absence of a particular biological process, a constant measurement may indicate occurrence of that process. Marker measurements can be represented in absolute or relative values (e.g. the relative concentration of two molecules in a biological sample). As used herein, a reference to a "marker" includes a combination of two or more such markers.

In the context of the present invention, expression of a beta tubulin isotype would be referred to as "higher" in for example activated endothelial cells compared to quiescent endothelial cells if the method for detecting expression of the beta tubulin isotype indicates that the level or activity of the isotype is higher or greater in the activated cells compared to the quiescent cells (or if the isotype is detectable in the activated cell but not in the quiescent cell).

The increase in expression may be measured by any method or technique known to those of skill in the art. As will be appreciated by one of skill in the art, the observed increase may vary depending on the particular method or technique that is used to make the measurement. For example, the difference in the level of expression or activity of a beta tubulin isotype between two samples (e.g. between an activated endothelial cell and a quiescent endothelial cell) can be measured at the transcriptional level, i.e. the conversion of the information encoded in the gene into messenger RNA (mRNA), at the translational level, i.e. the conversion of mRNA to protein, or a combination of both.

Changes in expression or activity of a beta tubulin isotype can be measured by any method known in the art. Such commonly used methods include differential display (Liang P et al., 1992, *Science* 257(5072): 967), representational difference analysis (Lisitsyn N A et al., 1993, *Science* 259(5097): 946), serial analysis of gene expression (Velculescu V E et al., 1995, *Science* 270(5235): 4484), and more recently array based technologies (Schena M et al., 1995, *Science* 270(5235): 467).

By way of example only the step of determining differential expression of a beta tubulin isotype at the transcriptional level may be carried out by detecting the presence of mRNA by reverse transcription polymerase chain reaction (RT-PCR), including quantitative RT-PCR, or using specific nucleic acid arrays utilising microchip technology. By way of example only the step of determining differential expression of a beta tubulin isotype at the translational level may be carried out by detection of the protein encoded by the mRNA, for example using ELISA, protein immunochemical analysis, proteomic arrays, or intracellular staining as detected by flow cytometry. All of these methods are well known in the art.

Essentially, a beta tubulin isotype which shows differential expression in activated compared to quiescent endothelial cells represent a marker for these cells, and allows the cell types to be distinguished and isolated from each other.

The present invention provides the use of a differentially expressed beta tubulin isotype in methods for identifying an agent which will selectively interact with activated or quiescent endothelial cells.

As used herein, the term "selectively interact" is taken to mean an agent which targets, binds to, or recognises one endothelial cell type, i.e. activated or quiescent, in preference to the other endothelial cell type. An agent which selectively interacts with activated endothelial cells will therefore be an agent which exhibits activity against activated endothelial cells, e.g. is able to modulate the function of these cells, at a lower concentration than its ability to modulate the function of quiescent endothelial cells. An agent will display selectivity for activated or quiescent endothelial cells if it has at least 5 to 100 times or greater preference for one cell type over the other. Selectivity of an agent can be determined by establishing its IC50 value, i.e. the concentration of the agent which causes a 50% reduction in a measured activity. Alternatively, the selectivity of the agent can be determined by establishing the EC50 value, i.e. the concentration of the agent that is required to obtain 50% of its maximum effect in vitro or in vivo.

An agent will selectively interact with activated endothelial cells due to the higher expression of a beta tubulin isotype within those cells. Alternatively, an agent will selectively interact with quiescent endothelial cells due to the higher expression of a beta tubulin isotype within the quiescent cells.

It has been demonstrated that development of cancer cell resistance to agents that target tubulin polymerisation correlates with the overexpression of certain tubulin isotypes (e.g. beta III expression correlates with resistance to paclitaxel). We hypothesise that the response to a therapeutic agent by endothelial cells is also likely to be influenced by the level of expression of certain tubulin isotypes, consequently expression of tubulin isotypes, including beta tubulin isotypes, can be predictive of agent efficacy.

Furthermore, given the diversity of pro-angiogenic growth factors released by different tumour cells it is likely that endothelial cells within different tumour types express different tubulin isotypes that may correlate with tumour type and/or stage of progression.

Therefore the present invention enables the use of a differentially expressed beta tubulin isotype as a marker which can be used to predict a response to a therapeutic and/or to monitor disease progression.

Since endothelial cells play an integral role in angiogenesis and/or vascular function, the present invention also enables the use of a differentially expressed beta tubulin isotype in methods for identifying an agent which can affect these processes, and therefore have utility in the prophylaxis or treatment of angiogenesis-related disorders or conditions.

The term "vascular function" as defined herein, refers to the conductance of blood into and from various organs/tissues which are under normal or pathogenic circumstances. The term encompasses pre-established blood vessel networks such as those present in established tumours, rather than encompassing the formation of new blood vessels.

The term "angiogenesis" as used herein, refers to the formation of new blood vessels (also referred to as neovascularisation), and/or the increase in the volume, diameter or length, or altering the permeability of existing blood vessels, such as blood vessels in a tumour or between a tumour and surrounding tissue.

The angiogenic process is highly dynamic, often requiring coordinated spatial and temporal waves of gene expression. Due to its complex nature, the process of angiogenesis is subject to disruption through interference with one or more critical steps, and numerous disease states or conditions can result from, or be exacerbated by, an increase or decrease in angiogenesis.

Examples of angiogenesis-related disorders or conditions which are the result of uncontrolled or enhanced angiogenesis, or in which decreased vasculature is of benefit, include, but are not limited to, cancer, tumour growth and tumour metastases which require neovascularization, age-related macular degeneration (wet or dry form), diabetic retinopathy and other proliferative retinopathies including retinopathy of prematurity, retinal vascular disorders, macular disorders, cardiovascular disease, capillary proliferation in atherosclerotic plaques and osteoporosis, aberrant hypertrophy, arthritis, rheumatoid arthritis, osteoarthritis, chronic articular rheumatism, psoriasis, psoriatic plaques, sarcoidosis, atherosclerosis, atherosclerotic plaques, oedema from myocardial infarction, uveitis, retinitis, retinitis pigmentosa, choroiditis, retrolental fibroplasia, neovascular glaucoma, diabetic macular oedema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, lung inflammation, acute lung injury/acute respiratory distress syndrome (ARDS), sepsis, hypertension (e.g., primary pulmonary hypertension), malignant pulmonary effusions, cerebral oedema (e.g., associated with acute stroke/closed head injury/trauma), synovial inflammation, pannus formation in rheumatoid arthritis, myositis ossificans, hypertrophic bone formation, refractory ascites, polycystic ovarian disease, endometriosis, 3rd spacing of fluid diseases (pancreatitis, compartment syndrome, burns, bowel disease), uterine fibroids, premature labor, chronic inflammation such as inflammatory bowel disease (Crohn's disease and ulcerative colitis), renal allograft rejection, nephrotic syndrome, undesired or aberrant benign tissue mass growth, obesity, adipose tissue mass growth, haemophilic joints, hypertrophic scars, inhibition of hair growth, Osier-Weber syndrome, pyogenic granuloma, retrolental fibroplasias, scleroderma, trachoma, vascular adhesions, synovitis, dermatitis, preeclampsia, ascites, pericardial effusion (such as that associated with pericarditis), pleural effusion, gastrointestinal ulceration, chronic airway inflammation and vasculitis. For example, ocular neovascularization has been implicated as the most common cause of blindness in adults, and underlies the pathology of approximately 20 eye diseases, including both the wet and dry forms of macular degeneration. In diabetic retinopathy, new capillaries formed in the retina invade the vitreous humour, causing bleeding and blindness. In certain previously-existing conditions such as rheumatoid arthritis and osteoarthritis, newly-formed capillary blood vessels invade the joints and destroy cartilage.

Examples of cancers may also include, without limitation, transformed and immortalized cells, solid tumours, myeloproliferative diseases, blastomas, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, serous adenocarcinoma, endometrioid adenocarcinoma, clear cell adenocarcinoma, mucinous adenocarcinoma, Brenner tumour, teratoma, dysgerminoma, choriocarcinoma, fibroma, granulosa cell tumour, Sertoli-Leydig cell tumour, undifferentiated ovarian carcinoma, salivary gland carcinoma, kidney or renal cancer, prostate cancer, vulval cancer, thyroid cancer, hepatic carcinoma, anal carcinoma, penile carcinoma, cancer of the head and/or neck, Ewing's sarcoma, hemangiosarcoma, Kaposi's sarcoma, liposarcoma, peripheral neuroepithelioma, synovial sarcoma, Hodgkin's disease, etc. as known in the art.

Examples of angiogenesis-related disorders or conditions which are the result of inappropriately arrested or decreased angiogenesis, or in which increased vasculature is of benefit include, but are not limited to, wound healing, hair growth, formation and growth of the corpus luteum during pregnancy, restoration of tissue structure and function after injury, ischemic limb disease, myocardial ischemia, and coronary artery disease.

As used herein, the term "agent" includes, but is not limited to, peptides, small organic compounds, antibodies, and antisense/gene silencing agents.

Peptides may be in the form of peptide libraries which can be screened without undue experimentation using well known techniques. For example, assays for screening peptide libraries for peptides which bind to a polypeptide target are well known in the art (see U.S. Pat. Nos. 5,556,762, 5,750, 373, 4,708,871, 4,833,092, 5,223,409, 5,403,484, 5,571,689, 5,663,143; and PCT Publication Nos. WO 84/03506 and WO84/03564).

Bacteriophage (phage) display libraries are commonly screened. Phage display is a technique by which variant polypeptides are displayed as fusion proteins to the coat protein on the surface of bacteriophage particles (Scott J K and Smith G P, 1990, *Science* 249: 386). The utility of phage display lies in the fact that large libraries of selectively randomized protein variants (or randomly cloned cDNAs) can be rapidly and efficiently sorted for those sequences which bind to a target molecule with high affinity.

Although most phage display methods use filamentous phage, lambdoid phage display systems, T4 phage display systems and T7 phage display systems are also known in the art. Many other improvements and variations of the basic phage display concept have also been developed. These improvements enhance the ability of display systems to screen peptide libraries for binding to selected target molecules and to display functional proteins with the potential of screening these proteins for desired properties.

An agent in the form of an antibody can be identified by screening antibody phage libraries. Phage can be utilized to display antigen-binding domains expressed from a repertoire or combinatorial antibody library (e.g., human or murine). Phage expressing an antigen binding domain that binds the antigen of interest, e.g. a differentially expressed beta tubulin isotype, can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Exemplary methods are set forth, for example in U.S. Pat. No. 5,969,108. In phage display methods, functional antibody domains are displayed on the surface of phage particles which carry the polynucleotide sequences encoding them. In particular, DNA sequences encoding $V_H$ and $V_L$ regions are amplified from animal cDNA libraries or synthetic cDNA libraries. After phage selection, the antibody coding regions from the phage can be isolated and used to generate whole antibodies, including human antibodies, or any other desired antigen binding fragment, Small organic compounds are usually less than about 2000 daltons in size, alternatively less than about 1500, 750, 500, 250 or 200 daltons in size. Small organic compounds may include, but are not limited to, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

Small organic compounds as part of chemical libraries may be screened, or may be synthesized using known methodology (for example see PCT Publication Nos. WO00/00823 and WO00/39585). Techniques for screening small organic compound libraries that are capable of binding to a polypeptide target are well known in the art (see PCT Publication Nos. WO00/00823 and WO00/39585).

Antisense/gene silencing agents include antisense oligonucleotides, and antisense RNAs such as short interfering RNA (siRNA) molecules. As will be understood by the person skilled in the art, an siRNA is a short sequence of RNA which is the complement of a segment of a transcribed RNA and consequently binds thereto, and, in so doing, modulates or silences expression of a gene in question.

An siRNA molecule used to modulate or silence a gene in question may be in the form of single-stranded antisense, double-stranded antisense or double-stranded antisense with chemical modifications.

As used herein, the terms "inhibit" or "promote", or "inhibiting" or "promoting", are taken to mean the ability of an identified agent to cause an overall decrease or increase, respectively, preferably of 20% or greater, more preferably of 50% or greater, and most preferably of 70%, 75%, 85%, 90%, 95%, or greater.

In the context of angiogenesis and vascular function, "inhibit" or "promote" can refer to the size or number of blood vessels, the amount of blood vessel formation in angiogenic-related disorders, including vascular-related tumour growth, or the presence or size of metastases in cancer.

The ability of an agent to inhibit or promote angiogenesis and/or vascular function, or to selectively interact with activated or quiescent endothelial cells, can be measured by any method known in the art. For example assays which test for the effect that an agent has on one or more functional properties of the cells can be used. With respect to angiogenesis, such methods may exploit the cycle through which endothelial cells proceed during vessel formation, including proliferation, migration and capillary tube formation. With respect to vascular function, such methods may assay for the effect of an agent on established capillaries through use of capillary disruption assays. Other assays may examine the effect of an agent on the process of capillary tube formation on an extracellular basement membrane. For a recent review of appropriate assays, see Staton C A et al., (2004), *Int. J. Path.* 85: 233-248.

By way of example only, in vitro methods for examining the extent of inhibition or promotion of angiogenesis or vascular function may include endothelial cell and/or cancer cell and/or cancer cell line proliferation assays which determine net cell number, or assays which evaluate cell-cycle kinetics. Net cell number can be measured using a haemocytometer, or through measurement of the amount of formazan product produced from cleavage of 3-(4,5-dimethylthiazol-2-yl)-2,5-diphenyltetrazolium bromide by mitochondria present in living cells (Denizot F and Lang R, 1986, *J. Immunol. Methods* 89: 271-277; Wemme H et al., 1992, *Immunobiology* 185: 78-79). Alternatively, DNA synthesis is a measure of cell proliferation, and can be assayed by thymidine incorporation in endothelial cells, or by DNA-binding dyes. Cell-cycle kinetics is typically evaluated by using DNA-binding molecules such as bromodeoxyuridine coupled with flow cytometric analysis.

Endothelial cell migration assays measure the extent of endothelial cell chemotaxis in the presence of an agent. For example, modified Boyden chamber assays may be used (Alessandri G et al., 1983, *Cancer Res.* 43: 1790-1797), in which activated or quiescent endothelial cells are plated on top of a filter, and the extent of cell migration across the filter is measured in the presence of an agent which is placed in the lower chamber. Inhibition of the migration of activated endothelial cells across the filter indicates that the agent is anti-angiogenic in nature, whereas migration of quiescent cells across the filter indicates that the agent is pro-angiogenic in nature.

Endothelial cell migration into a denuded area on a surface can also be measured. Such a method is typically referred to as the scratch wound healing assay. In this assay, endothelial cell monolayers are prepared and a portion of the monolayer is scraped clear, i.e. wounded, of endothelial cells. The ability of the cells to migrate and fill the denuded area in the presence of an agent being tested can then be monitored microscopically (Pepper MS et al., 1990, *J. Cell Biol.* 111: 743-755).

In vitro methods that assay for the formation of capillary-like tubules by endothelial cells are also suitable for evaluating inhibition or promotion of angiogenesis by an agent or for measuring the ability of an agent to selectively interact with activated or quiescent endothelial cells. Such differentiation assays usually involve the culturing of endothelial cells on matrices consisting of fibrin, collagen or Matrigel, which stimulate the attachment, migration and differentiation of endothelial cells into tubules in a manner that approximates the in vivo situation (Lawley T J and Kubota Y, 1989, *J. Invest. Dermatol.* 93: 59S-61S; Kanzawa S, 1993, *Ann. Plast. Surg.* 30: 244-251).

Organ culture assays, such as the aortic ring assay (Nicosia R F and Ottinetti A, 1990, *Lab. Invest.* 63: 115-122) and the chick aortic arch assay (Muthukkaruppan V R et al., 2000, *Proc. Am. Assoc. Cancer Res.* 41: 65), may also be used. In the rat aortic ring assay, an isolated rat aorta is cut into segments which are placed in culture, generally in a matrix-containing environment such as Matrigel. Over the next 7-14 days, the explants are monitored for the outgrowth of endothelial (and other) cells as this is affected by the addition of test agents. Quantification is achieved by measurement of the length and abundance of vessel-like extensions from the explant. Use of endothelium-selective reagents such as fluorescein-labeled BSL-I allows quantification by pixel counts.

In vitro cell-based assays, including those described above may, may employ endothelial cells which have been appropriately cultured to represent an activated or quiescent endothelial cell source, or may employ endothelial cells which have been stably transformed with recombinant nucleic acid molecules which over-express a beta tubulin isotype. For example, a cell-line which over-expresses beta I tubulin will be representative of activated endothelial cells. Similarly, a cell-line which over-expresses beta III tubulin will be representative of quiescent endothelial cells.

By way of example only, in vivo methods for examining the extent of inhibition or promotion of angiogenesis may include the subcutaneous implantation of a polymer matrix, for example in the form of a sponge or Matrigel plug, into an animal such as a mouse (Plunkett M L and Hailey J A, 1990, *Lab. Invest.* 62: 510-517; Dellian M et al., 1996, *Am. J. Pathol.* 149: 59-72). For measuring the extent of inhibition of angiogenesis, the matrix is impregnated with one or more angiogenesis-inducing factors together with an agent being tested. The extent of neovascularistion in the presence of the agent can then be assessed by a variety of methods commonly known in the art, such as immunohistological staining (for example the integrin status of vessels in the sponge, or detection of the CD31 antigen, a marker of angiogenesis); the blood/haemoglobin content of the sponge; or the levels of radioactive tracer in the blood (Mahadevan V et al., 1989, *Cancer Res.* 49: 415-419; Plunkett M L and Hailey J A, 1990, *Lab. Invest.* 62: 510-517). For measuring the ability of an agent to promote angiogenesis, angiogenesis-inducing factors are omitted from the matrix, and again the extent of neovascularisation is examined.

The chick chorioallantoic membrane assay (Nguyen M et al., 1994, *Microvasc. Res.* 47: 31-40; Ribatti D et al., 1996, *Int. J. Dev. Biol.* 40: 1189-1197), commonly referred to as the CAM assay, is also an appropriate in vivo assay for studying angiogenesis. An agent to be tested is first prepared either in slow-release polymer pellets, absorbed by gelatin sponges, or air-dried onto plastic discs. The pellets, sponges or discs may also comprise one or more angiogenesis-inducing factors, such as VEGF or basic fibroblast growth factor, depending on whether the agent is being tested for its ability to inhibit or promote angiogenesis. These are then implanted on to the CAM through a window cut in the shell of an embryonated chicken egg. After a suitable incubation period, the amount of blood vessel formation in the CAM in the presence of the agent can then be assessed using a stereomicroscope. A variation of this technique may also be used, in which shell-less chicken embryos are cultured in petri dishes prior to applying the agent.

Other suitable in vivo methods include the corneal angiogenesis assay (Gimbrone M A J et al., 1974, *J. Natl. Caner Inst.* 52: 413-427; Muthukkaruppan V R and Auerbach R, 1979, *Science* 205: 1416-1418) such as the rabbit corneal pocket assay, the dorsal air sac model (Oikawa T et al., 1997, *Anticancer Res.* 17: 1881-1886; Yonekura K et al., 1999, *Clin. Cancer Res.* 5: 2185-2191; Semba T et al., 2004, *Clin. Cancer Res.* 10: 1430-1438), and chamber assays such as the rabbit ear chamber (Dudar T E and Jain R K, 1983, *Microvasc. Res.* 25: 1-21; Gerlowski L and Jain R K, 1986, *Microvasc. Res.* 31: 288-305), dorsal skin chamber (Leunig M et al., 1992, *Cancer Res.* 62: 6553-6560; Dellian M et al., 1996, *Am. J. Pathol.* 149: 59-72), and cranial window assay (Levasseur J E et al., 1975, *Stroke* 6: 308-317).

Tumour models can also serve as suitable in vivo systems to examine the inhibition of angiogenesis and/or vascular function by an agent. Tumours can be grown in a suitable host syngeneically, orthotopically (in the tissue of origin), or as xenografts in immunodefficient mice, and the effect of an agent on tumour growth and host survival determined (Stribbling S M et al., 2000, *Hum. Gene. Ther.* 11: 285-292; Brown N J et al., 2002, *Br. J. Cancer* 86: 1813-1816; Tercel M et al., 2003, *J. Medicinal. Chem.* 46: 2132-2151; Staton C A et al., 2004, *Blood* 103: 601-606). The growth of tumours beyond a certain size is dependent on the development of blood vessels (i.e. angiogenesis), which serve to feed the tumour oxygen and nutrients, and remove waste products. Histological assays can therefore be used to assess the effects of an agent on the formation of these new vessels in tumour models.

The ability of an agent to inhibit or promote angiogenesis and/or vascular function, or to selectively interact with an activated or quiescent endothelial cell, can also be measured by assessing the effect of the agent on tubulin polymerisation in vitro. Suitable tubulin polymerisation assays are known in the art and are commercially available, for example the tubulin polymerisation kit from Cytoskeleton, Inc.

Essentially, the ability of tubulin to polymerize into microtubules in the presence of an agent can be followed by observing an increase in optical density of a tubulin solution at OD340 nm or by a change in the fluorescence. The absorbance-based assay (Shelanski M L et al., 1973, *PNAS* 70: 765-768) actually measures light scatter, wherein the greater the light scatter the less light reaches the detector. This assay is less sensitive to short microtubule formation which is under-represented in the initial stages of polymerization.

The fluorescence based assay (Bonne D et al., 1985, *J. Biol. Chem.* 280(5): 2819-2825) uses the fluorophore DAPI, which preferentially binds to the microtubule conformation of microtubules compared to the un-polymerized tubulin monomers.

Both assay formats create a similar kinetic polymerization profile. This profile is represented by a nucleation phase corresponding to the aggregation of tubulin monomers into protofilament or ring-like structures. These nucleation centres create a framework for more specific aggregation that elongates the protofilaments and closes a cylinder called the microtubule. Further microtubule elongation is represented by the polymerization phase, and when equilibrium is reached between the monomer and microtubule, the phase is referred to as the steady state.

There are a number of types of tubulin ligands. For example, there are those which bind to the monomer and inhibit its polymerization (e.g. vinblastine), and those which enhance polymerization (e.g. paclitaxel). Enhancing ligands decrease the nucleation phase, and increase the rate and extent of polymerization, i.e. a higher steady state value. In the case of monomer-binding ligands which inhibit polymerization, all phases are oppositely affected. Other tubulin ligands are distinguished based on their site of binding to tubulin. Differences in the amino acid sequence between tubulin isotypes at the site of binding of the agent will influence the affinity of the binding agent for a particular tubulin isotype.

The ability of an agent to inhibit or promote angiogenesis and/or vascular function, or to selectively interact with activated or quiescent endothelial cells, can also be measured using tubulin binding assays. For example, activated or quiescent endothelial cells, a cell-line over-expressing a beta tubulin isotype, or a differentially expressed beta tubulin isotype polypeptide, can be used to measure for the formation of complexes between an agent being tested and the relevant beta tubulin isotype.

The methods of the present invention are suitable for high-throughput screening.

Agents which selectively interact with activated endothelial cells and affect their function, and/or agents which bind to a beta tubulin isotype which shows increased expression in these cells (e.g. beta I tubulin) is considered an agent which may inhibit angiogenesis and/or vascular function, and therefore can be used for the treatment or prophylaxis of an angiogenesis-related disorder or condition which results from uncontrolled or enhanced angiogenesis, or a disease or condition in which decreased vasculature is of benefit. Similarly, agents which selectively interact with quiescent endothelial cells and affect their function, and/or agents which bind to a beta tubulin isotype which shows increased expression in these cells (e.g. beta III tubulin) is considered an agent which may promote angiogenesis and/or vascular function and therefore can be used for the treatment or prophylaxis of an angiogenesis-related disorder or condition which results from inappropriately arrested or decreased angiogenesis, or a disease or condition in which increased vasculature is of benefit.

The terms "treatment" and "prophylaxis" mean affecting a subject, tissue or cell to obtain a desired pharmacological and/or physiological effect and include:

(a) preventing the disorder or condition from occurring in a subject that may be predisposed to the disorder, but has not yet been diagnosed as having it;

(b) inhibiting the disorder or condition, i.e., arresting its development; or (c) relieving or ameliorating the effects of the disorder or condition, i.e., cause regression of the effects of the disorder or condition.

The term "subject" as used herein refers to any animal having a disorder or condition which requires treatment or prophylaxis with a pharmaceutically-active agent. The subject may be a mammal, preferably a human, or may be a non-human primate or a non-primate animal such as those used in animal model testing. While it is particularly contemplated that the agents of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids and ungulates.

It will be appreciated that agents which are identified by the methods described herein are within the scope of the invention.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

EXAMPLES

The invention is further described in detail by reference to the following experimental examples. These examples are provided for purposes of illustration only, and are not intended to be limiting unless otherwise specified. Thus, the invention encompasses any and all variations which become evident as a result of the teaching provided herein.

Example 1

The expression of tubulin isotypes beta I and beta III was examined at the transcriptional and translational level in activated and quiescent endothelial cells.

Human umbilical vein endothelial cells (HUVECs) were cultured overnight either in the presence (activated) or absence (quiescent) of growth factors. For example, for activated cells HUVECs were seeded at $6.25 \times 10^5$ cells/T75 flask in EGM-2 medium with growth supplements (Clonetics, USA, Basal EBM-2 medium, hEGF, Hydrocortisone, GA-1000 (gentamicin, amphotericin-B), 2% fetal bovine serum, vascular endothelial growth factor, human fibroblast growth factor-beta, $R^3$-insulin growth factor-1, Ascorbic acid, Heparin). For quiescent cells, HUVEC were seeded at $3.75 \times 10^6$ in EBM-2 basal medium (Basal EBM-2 medium, 0.1% GA-1000 (gentamicin, amphotericin-B), 0.5% FBS) with no growth supplements. Respective culture media were replaced the following day. Cells were incubated at 37° C., 5% $CO_2$ with humidity for 48 hours before harvesting.

For the transcriptional analysis, total RNA was isolated from quiescent and activated cells using the RNeasy Mini kit (Qiagen) according to the manufacturer's instructions. The isolated RNA was also treated with TURBO DNase (Ambion, Austin, Tex., USA) to remove genomic DNA contamination. Total RNA (1 µg/ml) was reverse transcribed using M-MLVH (Promega) according to the manufacturer's directions. Real-Time PCR was run on the RotorGene™2000 (Corbett Research). Primers used to detect expression of beta I tubulin were forward 5'-CCC CAT ACA TAC CTT GAG GCG A-3' (SEQ ID NO: 1) and reverse 5'-GCC AAA AGG ACC TGA GCG AA-3' (SEQ ID NO: 2), beta III tubulin 5'-ATG AGG GAG ATC GTG CAC AT-3' (SEQ ID NO: 3) and 5'-CCC CTG AGC GGA CAC TGT-3' (SEQ ID NO: 4). PCR reactions used AmpliTaq Gold enzyme (Applied Biosystems) and followed the manufacturer's instructions. Cycling conditions were typically 94° C. for 12 minutes, 35 cycles of 94° C. for 45 s, 60° C. for 60 s, 72° C. for 60 s, for 35 cycles followed by 10 minute final extension at 72° C. All data were normalised to the expression of the housekeeping gene POLR2K (RNA polymerase II), which was amplified using the primers 5'-AGG GGC TAA CAA TGG ACA CC-3' (SEQ ID NO: 5) and 5'-CCG AAG ATA AGG GGG AAC TAC T-3' (SEQ ID NO: 6).

For the translational analysis, protein was harvested from quiescent and activated cells using the following procedure. Cells were washed twice with PBS. Cells were lysed by incubation in modified RIPA buffer (50 mM Tris-HCl, pH 7.4, 1% NP-40, 0.25% Na-deoxycholate, 150 mM NaCl, 1 mM EDTA, 1x complete protease inhibitors (Roche)) with agitation at 4° C. for 15 minutes. Lysed cells were then centrifuged at 13000 rpm for 15 minutes and the supernatant collected.

The relative abundance of beta I tubulin and beta III tubulin was determined by densitometry of Western analysis using beta I- and beta III-specific antibodies respectively, and normalising to the abundance of a beta-actin control. Briefly, samples were prepared as follows: 5-10 µg total protein was electrophoresed using the NuPAGE® electrophossis system (Invitrogen, Carlsbad, Calif., USA). Proteins were electrophoresed on a NuPAGE® 4-12% Bis-tris Precast Polyacrylamide gel at 135V for 70 minutes in NuPAGE® MES SDS Running Buffer (Invitrogen) (Appendix 6.2). After electrophoresis, the proteins were transferred to Amersham Hybond™-C Extra nitrocellulose membrane (GE Healthcare, United Kingdom) at 30V for 60 minutes in transfer buffer. Membranes were then blocked in 5% skim milk/TBS-T overnight at 4° C. or 1 hour at room temperature. Membranes were washed 3 times in TBS-T, 5 minutes per wash. Membranes were then incubated in 1:500-1-50,000 dilution of specific antibodies; either anti-beta I tubulin (T7816, Sigma), anti-beta III tubulin (MMS-435P, Canvance) or anti beta-actin (A11126, Molecular Probes) for 60 minutes at room temperature or overnight at 4° C., antibodies were diluted in 5% skim milk/TBS-T or TBS-T. Membranes were washed 3 times in TBS-T for 5 minutes. Membranes were then incubated in 1:5,000 dilution of sheep anti-mouse horseradish peroxidase (HRP) conjugate (AP326P, Silenus, Melbourne, Australia) in 5% skim milk/TBS-T or TBS-T for 60 minutes. Membranes were washed 3 times in TBS-T (Appendix 6.2), 5 minutes per wash. Blots were developed using Amersham ECL Plus™ Western Blotting Detection Reagent (GE Healthcare, United Kingdom) according to manufacturer's instructions. Blots were visualised on the ImageMaster VDS-CL using the chemiluminescence sample tray (GE Healthcare, United Kingdom). Bands were quantified using image-J (NIH, USA) software, normalising to the abundance of beta-actin.

Figure 1:
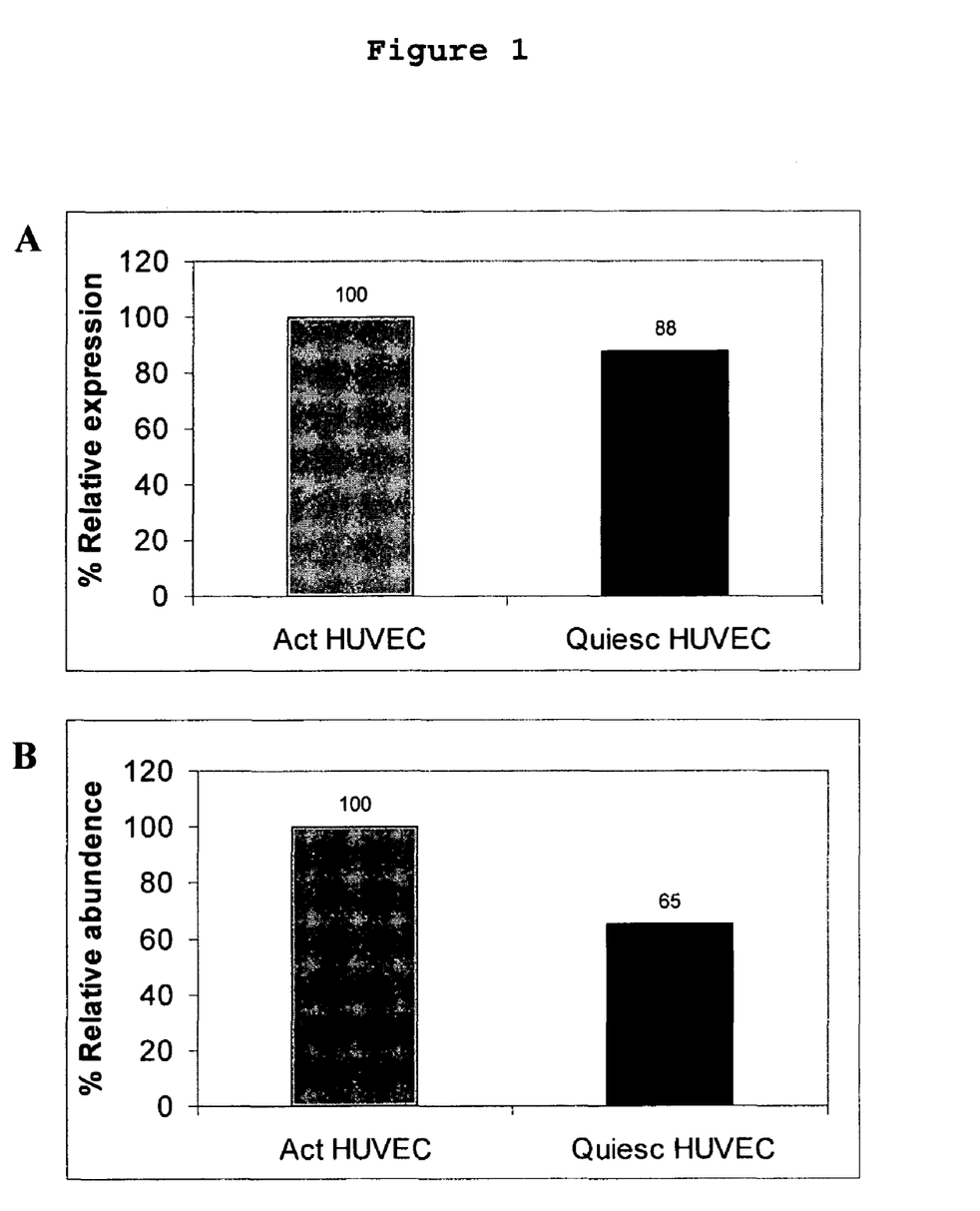
FIG. 1 shows a graphical result of expression of the beta I tubulin isotype RNA and protein in activated and quiescent human umbilical vein endothelial cells (HUVECs).
Figure 2:
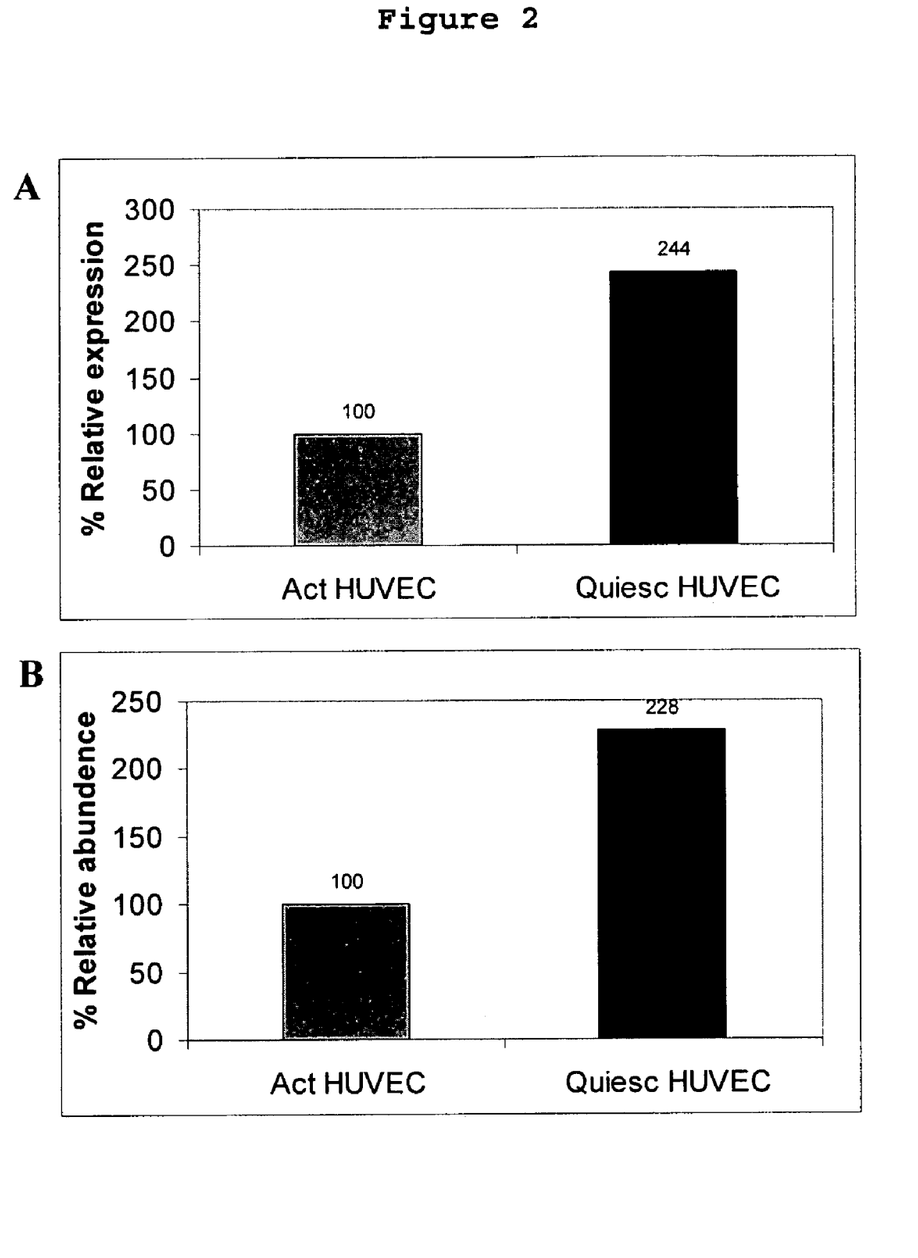
FIG. 2 shows a graphical result of expression of the beta III tubulin isotype RNA and protein in activated and quiescent HUVECs.

As can be seen in FIG. 1, activated HUVEC show an increase in beta I tubulin RNA (A) and protein (B) when compared to quiescent HUVEC. Furthermore, as shown in FIG. 2, quiescent HUVEC show increased beta III tubulin RNA (A) and protein (B) when compared to activated HUVEC.

Example 2

The expression of tubulin isotypes beta I and beta III was examined during capillary tube formation on a Matrigel matrix. 35 mm² wells of a microtitre plate were coated with 250 µl of matrigel (BD Biosciences) and incubated at 37° C. for 20 minutes. A second coat of 250 µl of matrigel was applied and then incubated at 37° C. for 20 minutes. HUVECs were seed at $3.33\times10^5$ cell per well. Cells were harvested at 0, 3, 6, 24 and 32 hrs. Cells were detached from matrigel by incubation with 40 caseinolytic units of dispase (BD biosciences) at 37° C. for 2 hours. The reaction was stopped by raising the EDTA concentration to 6.5 mM. Protein was then harvested and analysed via western blot as described above in Example 1.

Figure 3:
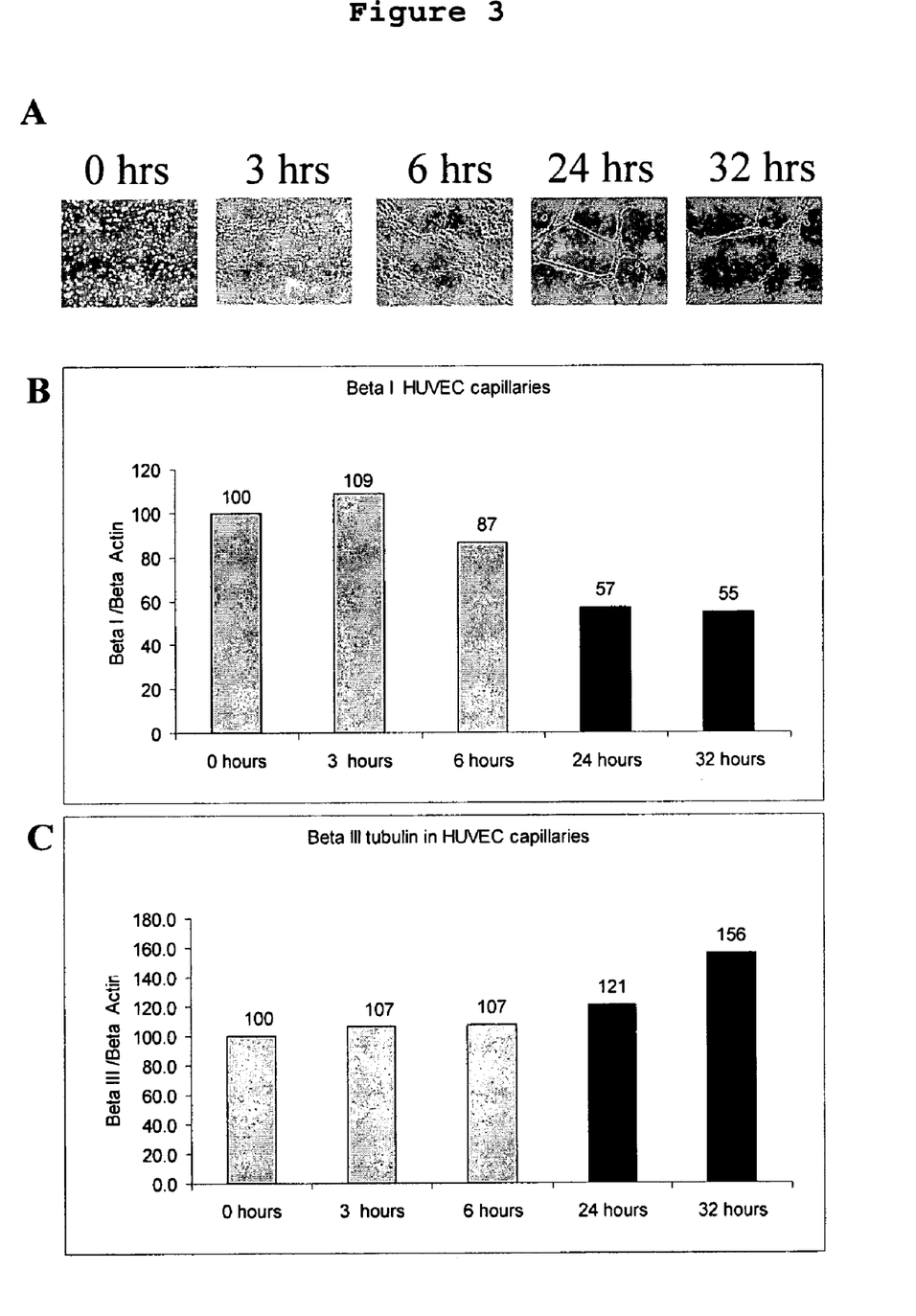
FIG. 3 shows a graphical result of the expression of tubulin isotypes beta I and beta III protein in activated and quiescent HUVECs during capillary tube formation on a Matrigel matrix.

FIG. 3A shows the extent of capillary tube formation at the time points 0, 3, 6, 24 and 32 hours. Endothelial cells are in the process of forming capillaries at the 0, 3 and 6 hour time points. Capillaries have formed by the 24 and 32 hour time points. As shown in FIG. 3B, HUVEC which are in the process of forming capillaries show an increase in beta I tubulin compared to cells which have formed capillaries and are in a resting or quiescent state. Furthermore, as shown in FIG. 3C, HUVEC that have formed capillaries and are resting show an increase in beta III tubulin when compared to the levels of beta III in cells which are still forming capillaries, i.e. are in an activated state.

The invention claimed is:

1. A method of identifying a candidate agent which inhibits angiogenesis, comprising:
   (a) providing activated endothelial cells in which beta I tubulin has higher expression compared to beta III tubulin;
   (b) adding a candidate agent to the activated endothelial cells in (a); and
   (c) determining the effect of the candidate agent on proliferation of the activated endothelial cells,
   wherein a candidate agent which suppresses proliferation of the activated endothelial cells is a candidate agent to inhibit angiogenesis.

2. A method of identifying a candidate agent which inhibits angiogenesis, comprising:
   (a) providing activated endothelial cells in which beta I tubulin has higher expression compared to beta III tubulin;
   (b) providing quiescent endothelial cells in which beta III tubulin has higher expression compared to beta I tubulin;
   (c) adding a candidate agent to the activated endothelial cells in (a);
   (d) adding a candidate agent to the endothelial cells in (b);
   (e) determining the effect of the candidate agent on proliferation of the activated endothelial cells; and
   (f) determining the effect of the candidate agent on proliferation of the quiescent cells;
   wherein a candidate agent which suppresses proliferation of the activated endothelial cells compared to the quiescent endothelial cells is a candidate agent to inhibit angiogenesis.

* * * * *